(12) United States Patent
Mastrorio et al.

(10) Patent No.: US 8,900,306 B2
(45) Date of Patent: Dec. 2, 2014

(54) NUCLEUS ANTI-EXPULSION DEVICES AND METHODS

(75) Inventors: Brooke W. Mastrorio, Lakeville, MA (US); Mark T. Hall, Bridgewater, MA (US); Shawn D. Stad, Fall River, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1242 days.

(21) Appl. No.: 11/535,413

(22) Filed: Sep. 26, 2006

(65) Prior Publication Data

US 2008/0097611 A1    Apr. 24, 2008

(51) Int. Cl.
*A61F 2/44* (2006.01)
*A61F 2/46* (2006.01)
*A61F 2/30* (2006.01)

(52) U.S. Cl.
CPC ......... *A61F 2/442* (2013.01); *A61F 2230/0013* (2013.01); *A61F 2230/0028* (2013.01); *A61F 2002/3008* (2013.01); *A61F 2002/30477* (2013.01); *A61F 2/4611* (2013.01); *A61F 2230/0065* (2013.01); *A61F 2002/30131* (2013.01); *A61F 2002/4495* (2013.01); *A61F 2250/0018* (2013.01); *A61F 2002/30014* (2013.01); *A61F 2002/30616* (2013.01); *A61F 2230/0004* (2013.01); *A61F 2220/0091* (2013.01); *A61F 2002/30135* (2013.01); *A61F 2002/30331* (2013.01); *A61F 2002/30841* (2013.01); *A61F 2002/30471* (2013.01); *A61F 2220/0033* (2013.01); *A61F 2220/0025* (2013.01); *A61F 2002/30166* (2013.01); *A61F 2002/30565* (2013.01); *A61F 2250/0098* (2013.01); *A61F 2002/30579* (2013.01); *A61F 2002/4435* (2013.01); *A61F 2002/30594* (2013.01); *A61F 2002/302* (2013.01); *A61F 2002/444* (2013.01)
USPC ..................... 623/17.16; 623/17.12

(58) Field of Classification Search
USPC ................. 623/16.11, 17.11–17.16
See application file for complete search history.

(56) References Cited

U.S. PATENT DOCUMENTS 6,224,630 B1 * 5/2001 Bao et al. .................. 623/17.16
6,245,107 B1   6/2001 Ferree
(Continued)

FOREIGN PATENT DOCUMENTS

WO    WO-02/17810 A2    3/2002
WO    WO-03/067341 A2   8/2003
(Continued)

OTHER PUBLICATIONS

URobotics, Brady Urological Institute, Johns Hopkins Medical Institutions, "PAKY Needle Driver" brochure (4 pp.).

(Continued)

*Primary Examiner* — Mary Hoffman
*Assistant Examiner* — Tara Carter
(74) *Attorney, Agent, or Firm* — Nutter McClennen & Fish LLP (57) ABSTRACT

Devices and methods for preventing the migration or expulsion of a nucleus disc replacement implant are provided. In one embodiment, an anti-expulsion device includes a body that is movable between a compressed configuration where it is adapted to fit through an opening in an annulus of a spinal disc, and an expanded configuration where it has a size that is larger than a size of the opening in the annulus of a spinal disc. The body can also include one or more mating features that allow the body to interact with a nucleus disc replacement implant and/or an annular wall of an annulus. As a result, since the body is larger than the opening of the annulus in the expanded configuration, the interlocking connection between the body and the nucleus disc replacement implant and/or annular wall will allow the body to prevent the nucleus disc replacement implant from being expulsed from the opening in the annulus.

24 Claims, 10 Drawing Sheets

(56) References Cited

U.S. PATENT DOCUMENTS

| | | | |
|---|---|---|---|
| 6,340,369 B1 | 1/2002 | Ferree | |
| 6,352,557 B1 | 3/2002 | Ferree | |
| 6,371,990 B1 * | 4/2002 | Ferree | 623/17.16 |
| 6,395,034 B1 * | 5/2002 | Suddaby | 623/17.15 |
| 6,400,979 B1 | 6/2002 | Stoianovici et al. | |
| 6,419,702 B1 | 7/2002 | Ferree | |
| 6,425,919 B1 | 7/2002 | Lambrecht | |
| 6,428,576 B1 * | 8/2002 | Haldimann | 623/17.16 |
| 6,443,960 B1 | 9/2002 | Brabrand et al. | |
| 6,454,804 B1 | 9/2002 | Ferree | |
| 6,468,311 B2 * | 10/2002 | Boyd et al. | 623/17.16 |
| 6,482,235 B1 | 11/2002 | Lambrecht et al. | |
| 6,508,839 B1 | 1/2003 | Lambrecht et al. | |
| 6,530,933 B1 * | 3/2003 | Yeung et al. | 606/151 |
| 6,592,625 B2 * | 7/2003 | Cauthen | 623/17.16 |
| 6,620,196 B1 * | 9/2003 | Trieu | 623/17.16 |
| 6,645,247 B2 | 11/2003 | Ferree | |
| 6,648,918 B2 | 11/2003 | Ferree | |
| 6,648,919 B2 | 11/2003 | Ferree | |
| 6,648,920 B2 | 11/2003 | Ferree | |
| 6,689,125 B1 | 2/2004 | Keith et al. | |
| 6,712,853 B2 | 3/2004 | Kuslich | |
| 6,883,520 B2 | 4/2005 | Lambrecht et al. | |
| 2002/0029083 A1 * | 3/2002 | Zucherman et al. | 623/17.16 |
| 2002/0029084 A1 * | 3/2002 | Paul et al. | 623/23.63 |
| 2003/0114930 A1 * | 6/2003 | Lim et al. | 623/17.11 |
| 2003/0199979 A1 * | 10/2003 | McGuckin, Jr. | 623/17.11 |
| 2004/0024463 A1 * | 2/2004 | Thomas et al. | 623/17.16 |
| 2004/0097980 A1 * | 5/2004 | Ferree | 606/151 |
| 2004/0186573 A1 | 9/2004 | Ferree | |
| 2004/0260397 A1 | 12/2004 | Lambrecht et al. | |
| 2004/0267366 A1 * | 12/2004 | Kruger | 623/17.16 |
| 2005/0015151 A1 * | 1/2005 | Fortin et al. | 623/17.13 |
| 2005/0038519 A1 | 2/2005 | Lambrecht et al. | |
| 2006/0089646 A1 | 4/2006 | Bonutti | |
| 2007/0043374 A1 | 2/2007 | Evans | |
| 2007/0276491 A1 * | 11/2007 | Ahrens et al. | 623/17.11 |
| 2008/0097611 A1 | 4/2008 | Mastrorio et al. | |

FOREIGN PATENT DOCUMENTS

| | | |
|---|---|---|
| WO | WO-2003/091839 A3 | 11/2003 |
| WO | WO-2004060202 A2 | 7/2004 |
| WO | WO-2004069026 A2 | 8/2004 |

OTHER PUBLICATIONS

URobotics, Brady Urological Institute, Johns Hopkins Medical Institutions, "The RCM Robot" brochure (2 pp.)

URobotics, Brady Urological Institute, Johns Hopkins Medical Institutions, "Z-Stage PAKY" brochure (1 pg.).

"Robopsy Design Project", Massachusetts Institute of Technology brochure (4 pp.).

Stoianovici, et al., (1997), "A Novel Mechanical Transmission Applied to Percutaneous Renal Access", Proceedings of the ASME Dynamic Systems and Control Division, DSC—vol. 61, pp. 401-406.

Maurin, B., et al., 2004, "A parallel 5 DOF positioner for semi-spherical workspaces", In Proceedings of the 2004 ASME Design Engineering Technical Conferences and Computer and Information in Engineering Conference, DETC2004-57406.

Maurin, B., et al., "A parallel robotic system with force sensors for percutaneous procedures under CT-guidance", Medical image computing and computer assisted intervention (MICCAI 04), St-Malo, France, Sep. 2004.

Maurin, B., et al., "A New Robotic System for CT Guided Percutaneous Procedure with Haptic Feedback", Computer Assisted Radiology and Surgery (CARS 04), Chicago, Jun. 2004.

International Search Report and Written Opinion for PCT/US07/18451 mailed May 19, 2008, 4 pages.

* cited by examiner

NUCLEUS ANTI-EXPULSION DEVICES AND METHODS

FIELD OF THE INVENTION

The present invention relates to devices and methods for replacing a nucleus of a spinal disc.

BACKGROUND OF THE INVENTION

A spinal disc is composed of two main parts, a gel-like inner portion called the nucleus pulposus, and a tough outer portion called the annulus fibrosus. The annulus is similar to a radial tire surrounding the nucleus. In a healthy disc, the nucleus is contained, and for the most part, centered within layers of the annulus, allowing for an even distribution of pressure thereby providing cushioning to the adjacent vertebrae surrounding the disc.

An artificial disc (also called a disc replacement, disc prosthesis or spine arthroplasty device) is a device that is implanted into the spine to imitate the functions of a natural disc (carry load and allow motion). There are many artificial disc designs classified into two general types: total disc replacement (TDR) and nucleus disc replacement (NDR). As the names imply, with a TDR, all or most of the disc tissue is removed and a replacement is implanted into the space between the vertebra. With an NDR, only the center of the disc (the nucleus) is removed and replaced with an implant. The outer part of the disc (the annulus) is not removed. NDR surgery offers certain benefits compared to TDR. Since an NDR device is designed to replace only the nucleus of the disc, the procedure is less destructive, possessing less risk and maintaining the functionality of surrounding structures, and it does not limit the possibility of a second surgery if one is needed.

One of the primary hurdles an NDR device has to overcome is the ability to stay within the annulus of the disc. In order to closely mimic the native nucleus, most NDR devices are made of soft and pliable biocompatible materials. One such material is called hydrogel, which expands as it absorbs water. The device is placed into the nucleus cavity of the disc and hydrates to expand and fill the cavity. The device is flexible or compressible and by this means, allows motion, much like a natural disc nucleus. In particular, the device can elastically deform during normal activities (axial loading, flexion, extension). While this motion is necessary for implant function, it also increases the likelihood that it is expulsed from the opening(s) formed in the annulus that are used to introduce the NDR into the annulus. Another issue is that the containment wall of the NDR is often a degenerated annulus that has existing or developing fissures in which the NDR device can expulse over time.

Accordingly, there remains a need for improved methods and devices for replacing the nucleus of a spinal disc, and in particular for containing the implant to prevent nucleus disc replacement expulsion.

SUMMARY OF THE INVENTION

The present invention generally provides devices and methods for replacing a nucleus of a spinal disc. In one embodiment an anti-expulsion device is provided that includes a body movable between a compressed configuration in which the body is adapted to fit through an opening in an annulus of a spinal disc, and an expanded configuration in which the body has a size larger than a size of the opening in the annulus of the spinal disc. The body can also include a mating feature that is adapted to interlock with at least one of a nucleus disc replacement implant and an annulus of a spinal disc to prevent expulsion of the nucleus disc replacement implant from the annulus of the spinal disc.

The body of the anti-expulsion device can have a variety of configurations. In one embodiment, the body can be substantially C-shaped in the expanded configuration with first and second ends. The mating feature can be, for example, at least one mating element that is formed on the first and second ends and that is adapted to interlock with at least one of a nucleus disc replacement implant and an annulus of a spinal disc. Exemplary mating elements can include curls, hooks, undercuts, penetrating legs, staples, coils, barbs, channels, holes, claws, and combinations thereof. In other embodiments, the mating feature can be in the form of a plug adapted to be positioned within an opening in an annulus, and the body can include legs coupled to the plug and adapted to be disposed within and to engage an inner wall of an annulus. The body can also include at least one bend region that facilitates movement of the body from the compressed configuration to the expanded configuration. While the bend region can be formed at a variety of locations on the body, in one exemplary embodiment the bend region can be formed at a mid-portion of the body such that the first and second ends of the body move toward one another in the compressed configuration. In another embodiment, the body can be substantially ring-shaped in the expanded configuration, and can include a central opening that is adapted to interlock with a nucleus disc replacement implant. In yet another embodiment, the body can be substantially spherical and can be formed from a mesh material that forms the mating feature.

The body of the device can also be adapted to facilitate reinforcement and/or regeneration of the annular wall. For example, in one embodiment, body can include a tissue regenerative material attached thereto or formed thereon, such as a bioactive or bioconductive tissue regenerative material. In another embodiment, the body can be adapted to reinforce an annular wall of an annulus of a spinal disc when the body is in the expanded configuration.

In another embodiment, a nucleus disc replacement system is provided that includes a nucleus disc replacement implant and an anti-expulsion device. The anti-expulsion device can include a body that is movable between a compressed configuration in which the body is adapted to fit through an opening in an annulus of a spinal disc, and an expanded configuration in which the body has a size that is larger than a size of an opening in an annulus of a spinal disc. The body of the device can be adapted to interlock with at least one of a nucleus disc replacement implant and an annulus of a spinal disc to prevent expulsion of the nucleus disc replacement implant through a hole in the annulus of a spinal disc. The device can have a variety of configurations, includes those discussed above.

Methods for implanting a nucleus disc replacement implant are also provided. In one embodiment, a method for implanting a nucleus disc replacement implant includes inserting an anti-expulsion device through an opening formed in an annulus of a spinal disc to position the anti-expulsion device within a nucleus void formed in a nucleus of the spinal disc. The anti-expulsion device can be in a compressed configuration during insertion. The method can also include releasing a force on the anti-expulsion device such that it moves from the compressed configuration to an expanded configuration in which the anti-expulsion device has a size greater than a size of the opening in the annulus to prevent expulsion of the nucleus disc replacement implant through the opening. The method can further include inserting a nucleus disc replacement implant into the nucleus void. In certain embodiments, the nucleus disc replacement implant can interlock with the anti-expulsion device. In another embodiment, the anti-expulsion device can be positioned against the opening in the annulus to reinforce the annular wall. Additionally or alternatively, the anti-expulsion device can include a tissue regenerative material that facilitates regeneration of the annular wall.

While a variety of techniques can be used to insert the anti-expulsion device into the annulus, in one embodiment the anti-expulsion device can be inserted through a cannula that compresses the anti-expulsion device into the compressed configuration. The device can then be advanced out of the cannula and into the annulus, causing the force on the device to be released. As a result, the anti-expulsion device moves from the compressed configuration to the expanded configuration and expands to a size that is larger than the opening within the annulus. By way of non-limiting example, when the anti-expulsion device is substantially C-shaped having opposed ends, the opposed ends can be moved toward one another when the anti-expulsion device is in the compressed configuration, and the ends can move away from one another when the force is released and the device moves to the expanded configuration.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for replacing at least a portion of a nucleus of a spinal disc, and in particular for preventing nucleus disc replacement implant expulsion. At least a portion of the natural nucleus of a spinal disc can be removed from the annulus by forming a small opening in the annulus. Once the desired portion of the nucleus is removed to form a nucleus void, one or more nucleus anti-expulsion devices can be implanted within the nucleus void either before, simultaneously with, or after the placement of a nucleus disc replacement implant. In an exemplary embodiment, the nucleus anti-expulsion device is configured to be inserted in a compressed configuration, and to expand once positioned within the nucleus void. The anti-expulsion device can interact with a nucleus disc replacement implant or the annulus to prevent expulsion of the implant from the annulus. In certain exemplary embodiments, the interaction between the anti-expulsion device and the nucleus disc replacement implant can be mechanical to provide a secure mating connection between the nucleus disc replacement and the anti-expulsion device. For example, the anti-expulsion device can have a configuration that will allow a nucleus disc replacement implant that is introduced into the nucleus void of the spinal disc to encapsulate, to be disposed around, to mate to, to adhere to, or to otherwise interlock with at least a portion of the anti-expulsion device, such that the anti-expulsion device and the nucleus disc replacement implant become integral with one another. In other embodiments, the anti-expulsion device can additionally or alternatively have a configuration that allows it to reinforce the annular wall and/or facilitate regeneration of the annular wall, and thereby prevent expulsion of the nucleus disc replacement implant.

While the various anti-expulsion devices disclosed herein can be used with a variety of nucleus disc replacement implants, the nucleus disc replacement implant is preferably formed from a material that mimics the characteristics of a natural nucleus, and it preferably provides some or all of the resistance to compressive loads provided by a natural nucleus. In one exemplary embodiment, the nucleus disc replacement implant can be formed from a material that can be injected into the nucleus void. While various nucleus disc replacement materials are known in the art, exemplary materials include, for example, hydrogels, silicones, polyurethanes, acrylics, collagens, and adhesives (including cyanoacrylates and fibrin glue) that cure after being injected into the nucleus void, or into a container, such as a bag or balloon, that is disposable within the nucleus void. A person skilled in the art will appreciate that the anti-expulsion device can be pre-shaped to mate to the insert and/or can be expanded, cured, and/or inflated prior to or after the introduction through the nucleus void.

A person skilled in the art will further appreciate that the devices disclosed herein can be used with procedures where the entire nucleus is removed, as well as procedures where only a portion of the nucleus is removed, such as treatments for degenerative disc diseases (e.g., disc herniation). By way of non-limiting example, where only some of the internal nucleus is removed, the nucleus anti-expulsion device can be used with just enough injectable in situ curing or adhesive material to fill the void of the internally removed nucleus.

FIGS. 1-18 illustrate various exemplary anti-expulsion devices that can be used to prevent migration or expulsion of a nucleus disc replacement implant from an annulus of a spinal disc. In general, each anti-expulsion device includes a body that is movable between a compressed configuration where it is adapted to fit through an opening in an annulus of a spinal disc and to fill a nucleus void created within the nucleus, and an expanded configuration where it has a size that is larger than a size of the opening in the annulus of a spinal disc. The body can also include one or more mating features that allow the body to interact and become integral with a nucleus disc replacement implant and/or an annulus. As a result, since the body is larger than the opening of the annulus in the expanded configuration, the interlocking connection between the body and the nucleus disc replacement implant and/or annulus will allow the body to prevent the nucleus disc replacement implant from being expulsed from the opening in the annulus.

The particular size of the body can vary. However, as noted above, the body is generally sized to fit through an opening in the annular wall when it is in the compressed configuration, and expands to a size that is greater than the size of the opening in the annular wall when it is within the nucleus void and is in the expanded configuration. By way of non-limiting example, when the body is in the compressed configuration it can have a maximum width of less than about 6 mm, and when it is in the expanded configuration it can have a maximum width that is greater than about 10 mm, and more preferably that is in the range of about 10 mm to about 30 mm. In certain exemplary embodiments, the dimensions of the body are in the range of about 5 mm to 50 mm. Additionally, the body can have a size that allows it to act as a reinforcement for the annular wall. For example, the body can be sized to match the curvature of the posterior wall of the annulus. Exemplary dimensions for such a configuration include a height in the range of about 7 mm to 15 mm, and a radius of about 10 mm to 30 mm. A person skilled in the art will appreciate that the particular dimensions of the anti-expulsion device can vary depending on the size of the nucleus void as well as the particular procedure being performed.

Turning first to FIGS. 1-5, various exemplary embodiments of an anti-expulsion device 10, 110, 210, 310 are shown having a body 12, 112, 212, 312 that is substantially C-shaped with two opposed distal ends 14, 16, 114, 116, 214, 216, 314, 316. Each distal end 14, 16, 114, 116, 214, 216, 314, 316 can include a mating element 18, 20, 118, 120, 218, 220, 318, 320 formed thereon for interlocking with a nucleus disc replacement implant and/or with an annular wall of an annulus. In use, each device 10, 110, 210, 310 can be inserted into the nucleus void of a spinal disc in a compressed configuration, and once within the nucleus void, each device 10, 110, 210, 310 can move to an expanded configuration where the size of the body 12, 112, 212, 312 is larger than the size of the opening in the annulus of a spinal disc.

Figure 1:
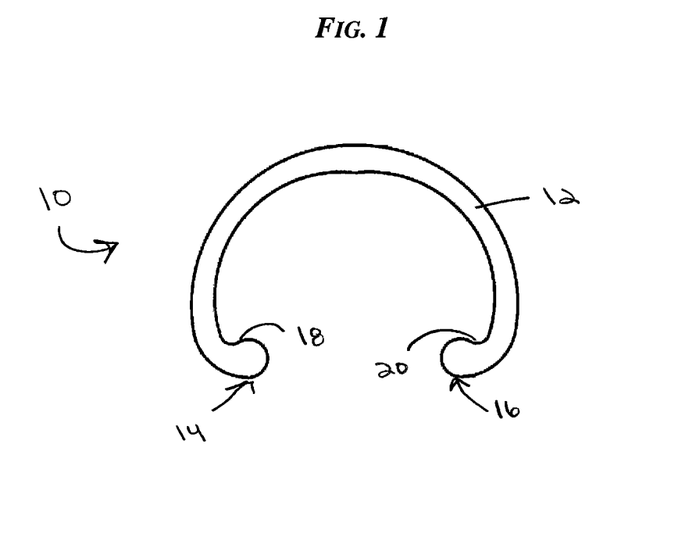
FIG. 1 is a top view of one exemplary embodiment of a nucleus anti-expulsion device.
Figure 2:
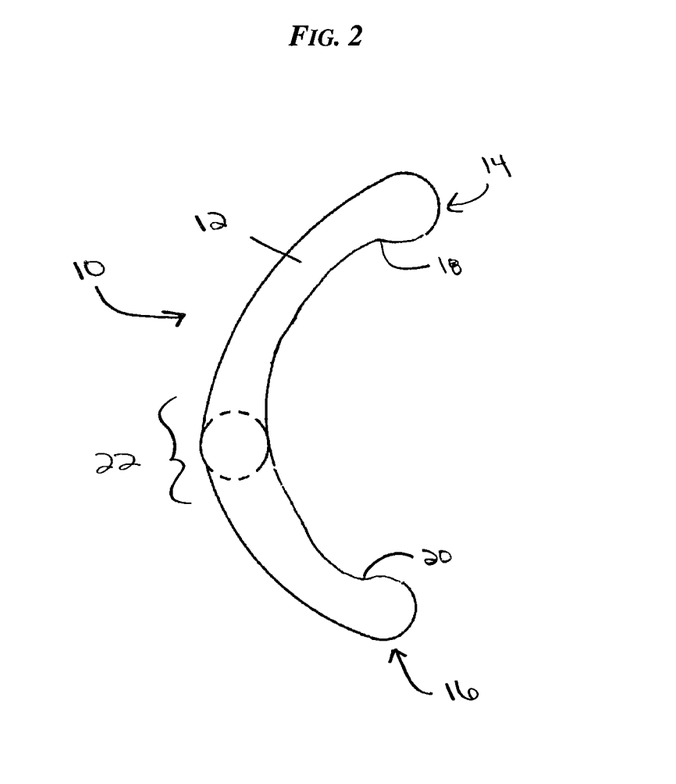
FIG. 2 is a top view of the nucleus anti-expulsion device of FIG. 1 showing a hinge formed thereon.
Figure 3:
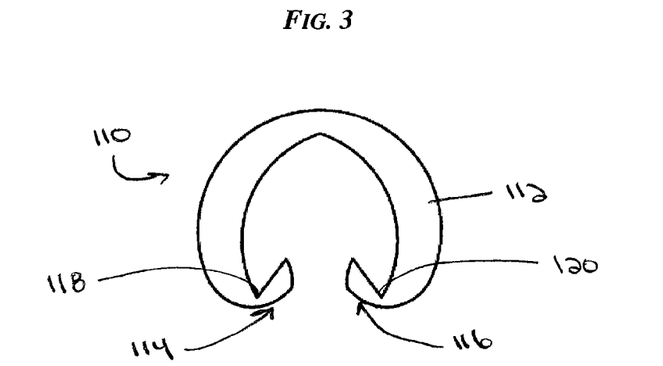
FIG. 3 is a top view of another embodiment of a nucleus anti-expulsion device having hooks formed thereon for mating with a nucleus disc replacement implant.
Figure 4:
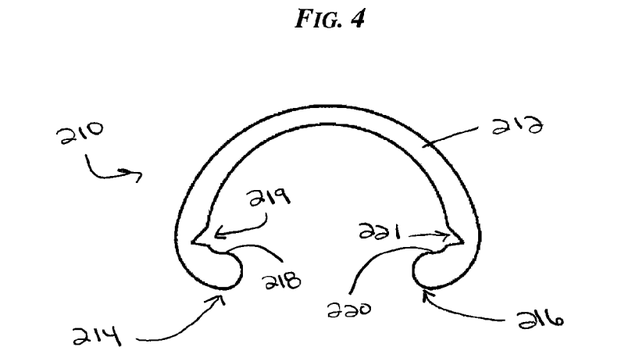
FIG. 4 is a top view of another embodiment of a nucleus anti-expulsion device having undercuts formed therein for mating with a nucleus disc replacement implant.
Figure 5:
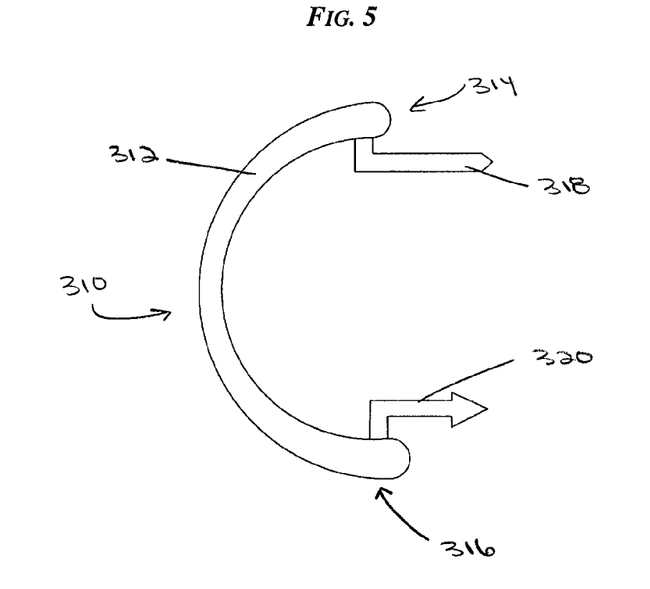
FIG. 5 is a top view of another embodiment of a nucleus anti-expulsion device having penetrating legs formed thereon for mating with a nucleus disc replacement implant.
Figure 6:
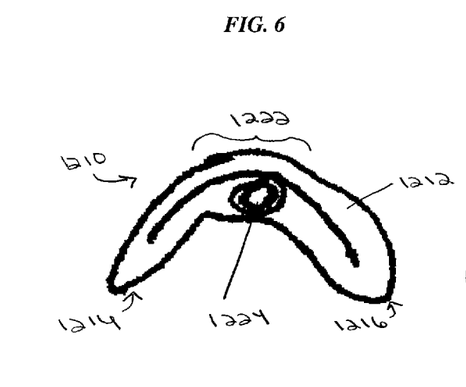
FIG. 6 is a top view of another embodiment of a nucleus anti-expulsion device having a bend region that includes a coil spring.

The mating elements on each device can have any configuration, and each device can include any number of mating elements formed at various locations on the body. In an exemplary embodiment, the mating element is effective to allow the body to interlock and become integral with a nucleus disc replacement implant. While the mating elements are described as interlocking with a nucleus disc replacement implant, a person skilled in the art will appreciate that the various mating elements can be used to allow the anti-expulsion device to interlock with the annular wall of the spinal disc. The devices 10, 110, 210, 310 of FIGS. 1-5 illustrate various exemplary mating elements. For example, FIGS. 1-2 illustrate a curled portion 18, 20 formed on the distal ends 14, 16 of the body 12. FIGS. 3-4 illustrate hooks 118, 120, 218, 220 that are formed on the distal ends 114, 116, 214, 216 of the body 112, 212. As shown in FIG. 4, the hooks 218, 220 can include undercuts 219, 221 that are formed in the body 212 adjacent to the distal ends 214, 216 thereof to further facilitate mating with a nucleus disc replacement implant. In another embodiment, as shown in FIG. 5, the mating elements 318, 320 can be in the form of penetrating legs or spikes 318, 320 that are formed on or coupled to the distal ends 314, 316 of the body 312. The legs 318, 320 can have a variety of configurations and can be preformed or precured. In other embodiments, the mating feature can be in the form of openings formed in the body, surface features formed on the body, or any other feature that will allow a nucleus disc replacement implant to interlock with the body. A person skilled in the art will appreciate that the mating elements can have a variety of other configurations in addition to those noted above, such as barbs, claws, coils, staples, channels, holes, or combinations thereof.

The body of the anti-expulsion device can also include features to facilitate movement of the device between the compressed configuration and the expanded configuration. In one embodiment, the device can include one or more bend regions that allow the device to be folded or otherwise compressed. While the bend region can be formed at a variety of locations on the body, FIG. 2 illustrates one embodiment of a bend region 22 formed at a mid-portion of the body 12 between the opposed distal ends 14, 16. This allows the ends 14, 16 to be moved together to decrease a maximum width of the body 12. While various techniques can be used to allow the body to bend, in the embodiment shown in FIG. 2 the bend region 22 is formed from a flexible material.

Figure 7:
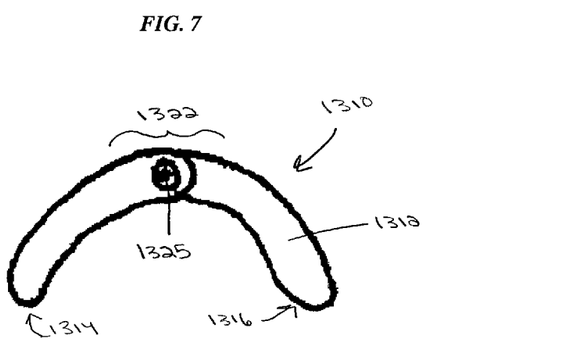
FIG. 7 is a top view of another embodiment of a nucleus anti-expulsion device having a bend region that includes a mechanical pivot point.
Figure 8:
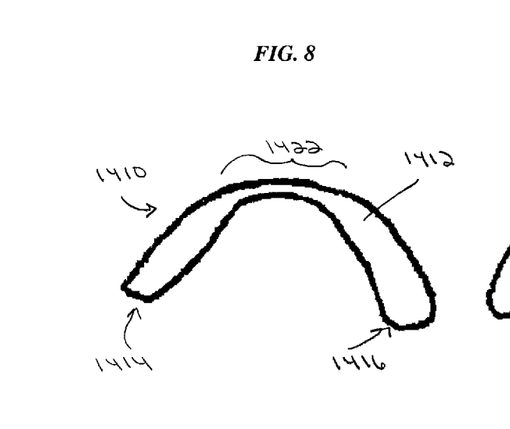
FIG. 8 is a top view of another embodiment of a nucleus anti-expulsion device having a bend region formed from a thinned region of material.
Figure 9:
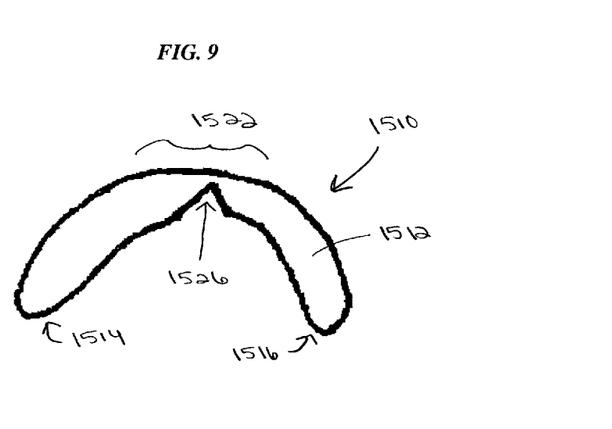
FIG. 9 is a top view of another embodiment of a nucleus anti-expulsion device having a bend region that includes a cut-out.

FIGS. 6-9 illustrate various other techniques for forming a bend region on the body. In the embodiment shown in FIG. 6, the device includes a coiled spring 1224 that is located at a mid-portion of the body 1212 between the opposed ends 1214, 1216 thereof. The coiled spring allows the ends 1214, 1216 to move toward one another. FIG. 7 illustrates a device 1310 where the bend region 1322 is formed by a mechanical pivot point or a hinge 1325 that is located at a mid-portion of the body 1312 between the opposed ends 1314, 1316 of the body 1312. FIG. 8 illustrates a device 1410 where the bend region 1422 is formed by a thinned portion of material that is located at the mid-portion of the body 1412 and between the opposed ends 1414, 1416 of the body 1412. A person skilled in the art will appreciate that the width of the thinned portion can vary depending upon the type of material that is used to form the body. In another embodiment, shown in FIG. 9, the bend region 1522 is formed from a cut 1526 formed in a mid-portion of the body 1512 between the opposed ends 1514, 1516 of the device 1510. The cut can have a variety of shapes, and its size and depth can vary depending upon the particular material used to form the body. In each of the various embodiments, the bend region can also be biased to the expanded configuration such that a force must be applied to the body 12 to move it to the compressed configuration. Upon release of the force, the body 12 can automatically return to the expanded configuration.

In use, a force can be applied to the body to deform or pivot the bend region, and thereby compress the body to decrease a maximum width of the body. For example, in the illustrated embodiments the opposed distal ends can be moved towards and optionally into contact with one another. This is particularly advantageous in that it allows the device to be inserted through an opening in the annular wall and to expand once disposed within the nucleus void to prevent expulsion of the device through the opening.

The body of the anti-expulsion device can also have a variety of other features. For example, the body can include one or more through holes formed therein that can be used to facilitate the implantation of the nucleus disc replacement implant. Following insertion of the anti-expulsion device into the nucleus void, the nucleus disc replacement implant can be injected through the through hole(s) of the device and into the nucleus void. This allows for integration of the anti-expulsion device and the nucleus disc replacement implant and/or overmolding of the anti-expulsion device.

A person skilled in the art will appreciate that the devices disclosed in FIGS. 1-9 can be formed from a variety of materials. In an exemplary embodiment, however, the body is preferably formed from a bioimplantable and flexible material. Exemplary materials can include pre-formed polymers, such as Teflon, polyurethane, and silicon, shape memory metals, such as nitinol, other metals, such as stainless steel and titanium, and combinations thereof. The device can also be formed from materials that allow for visualization thereof or that can be used to facilitate regeneration of the annular wall. For example, in one embodiment at least a portion of the device can be formed from a radiopaque material. This allows a surgeon to radiographically visualize the device to confirm intra-operative placement and/or to confirm placement during post-surgical follow-up. In another embodiment, the device can include tissue regenerative materials, such as bioactive or bioconductive regenerative materials in order to facilitate regeneration of the annular wall. The regenerative material can be incorporated into the materials used to form the device or it can be mated to or coated onto an outer surface of the device. Alternatively, the regenerative material can be in the form of one or more plugs that are inserted into at least a portion of the anti-expulsion device. While a variety of regenerative materials can be used with the devices disclosed herein, exemplary materials include, for example, small intestine submucosa (SIS) material, equine pericardium, growth/differentiation factor 5, bioactive proteins, and osteoconductive materials such as tricalcium phosphate and hydroxyapatite.

Figure 10A:
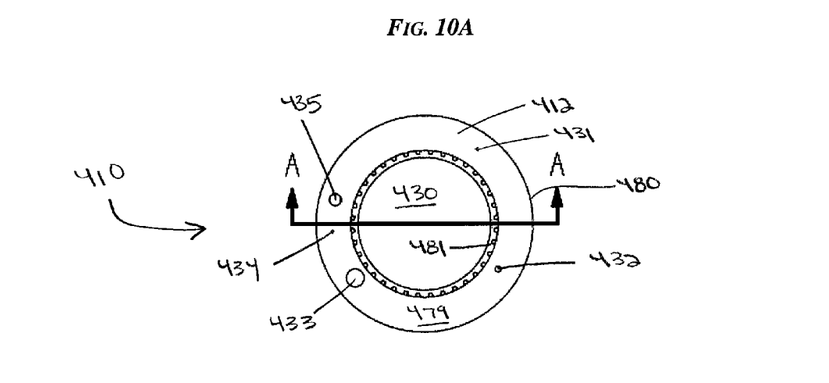
FIG. 10A is a top view of another embodiment of a nucleus anti-expulsion device having a ring-shaped configuration.
Figure 10B:
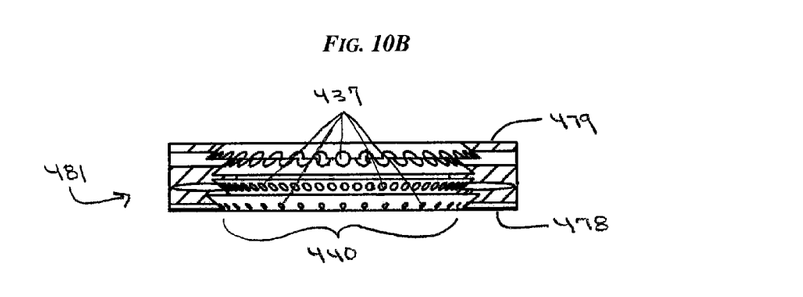
FIG. 10B is a cross-sectional view of the device of FIG. 10A taken across line A-A.

The anti-expulsion devices disclosed herein can have a variety of other configurations. FIGS. 10A-10B illustrate another embodiment of an anti-expulsion device 410 having a substantially ring-shaped body 412 with a central hole 430 formed therein. The body 412 can have a variety of widths and heights, and the particular size can vary depending upon the size of the nucleus void and the particular procedure being performed. For example, the body can have a height that spans across the disc space such that the body contacts the endplates of the adjacent vertebra. The body can also have a variety of cross-sectional geometries, as will be discussed in more detail below.

As further shown in FIG. 10, the anti-expulsion device 410 can include a variety of mating feature(s) that allow the device to mate to and become integral with a nucleus disc replacement implant and/or an annular wall. For example, in addition to the central hole 430, the body 412 can include one or more holes formed therein and extending therethrough. FIGS. 10A-10B illustrate holes 431, 432, 433, 434, 435 that extend between the superior and inferior surfaces 478, 479 of the body 412, as well as holes 437 that extend between the inner and outer surfaces 480, 481 of the body 412. The body can also or alternatively include teeth or other surface features formed on a variety of portions thereof to facilitate interlocking with the nucleus disc replacement implant. For example, FIG. 10B illustrates a saw-tooth geometry 440 that is formed on the inner surface 481 of the body 412. These additional mating elements further facilitate interlocking and subsequent integration between the anti-expulsion device 410 and the nucleus disc replacement implant.

Figure 11:
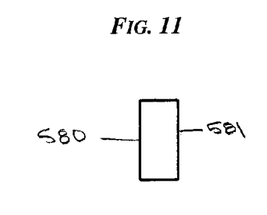
FIG. 11 is a cross-sectional view of another embodiment of a nucleus anti-expulsion device having a rectangular cross-sectional shape.
Figure 12:
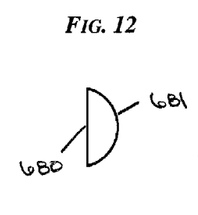
FIG. 12 is a cross-sectional view of another embodiment of a nucleus anti-expulsion device having a curved cross-sectional shape.
Figure 13:
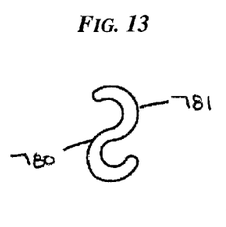
FIG. 13 is a cross-sectional view of another embodiment of a nucleus anti-expulsion device having an S-shaped cross-section.
Figure 14:
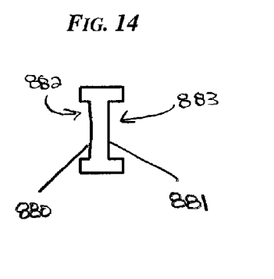
FIG. 14 is a cross-sectional view of another embodiment of a nucleus anti-expulsion device having an I-shaped cross-section.

As noted above, the cross-sectional shape of ring-shaped or c-shaped device can vary, and FIGS. 11-17 illustrate various other exemplary cross-sectional shapes. FIG. 11 illustrates a device having a substantially rectangular cross-sectional shape, where the inner and outer walls 580, 581 are substantially planar (or angled on one or more surfaces). FIG. 12 illustrates a device having a cross-sectional shape with a planar surface 680 and a curved or bowed surface 681. FIG. 13 illustrates another embodiment of a device that has a curved cross-sectional shape, however in this embodiment the device is substantially S-shaped with curved inner and outer surfaces 780, 781 for interlocking with a nucleus disc replacement implant. FIG. 14 illustrates a device having cut-outs 882, 883 formed on the inner and outer surfaces 880, 881 such that the device has an I-shaped cross-section that provides compression resistance. A person skilled in the art will appreciate that the cut-outs can have a variety of geometric shapes, and that the device can include various other features, such as those previously described herein, for facilitating mating between the anti-expulsion device and the nucleus disc replacement implant.

Figure 15:
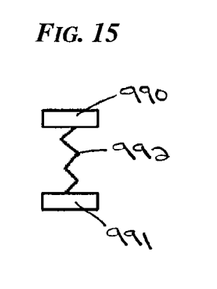
FIG. 15 is a cross-sectional view of another embodiment of a nucleus anti-expulsion device having two rings that are attached to one another by springs.
Figure 16:
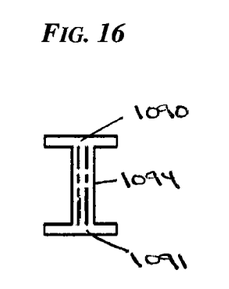
FIG. 16 is a cross-sectional view of another embodiment of a nucleus anti-expulsion device having two rings that are attached to one another by struts.
Figure 17:
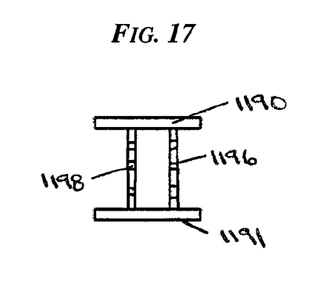
FIG. 17 is a cross-sectional view of another embodiment of a nucleus anti-expulsion device having two rings that are attached to one another by layers of mesh material.

While the devices of FIGS. 10A-14 illustrate a single ring, in other embodiments the device can also include multiple rings that are coupled to one another by one or more mating elements. By way of non-limiting example, FIGS. 15-17 illustrate various embodiments of devices having two rings that are attached to one another by one or more mating elements, such as struts or pegs. The first ring can be positioned adjacent to an endplate of a first vertebra and the second ring can be positioned adjacent to an endplate of a second adjacent vertebra such that the mating element span across the disc space between the adjacent vertebrae. The ring-shaped devices shown above in FIGS. 10A-17 can also be made from a variety of materials. Exemplary materials include biocompatible, flexible materials that allow the device to move between a compressed configuration for insertion into a nucleus void and an expanded configuration for release once positioned within the nucleus void. By way of non-limiting example, suitable materials include preformed polymers, such as Teflon, polyurethane, and silicon, fabrics such as polyethylene terephthalate (PET-Dacron), other polymeric or metallic fibers, and combinations thereof. The ring-shaped devices can also include radiopaque materials to facilitate visualization and/or regenerative materials for facilitating regeneration of the annular wall.

In the embodiment shown in FIG. 15, which illustrates a cross-section of the device, the first and second rings 990, 991 are connected by at least one spring 992. The spring can have a variety of configurations for interlocking with a nucleus disc replacement implant, such as curled, zig-zagged, or coiled. As shown, the spring 992 has a zig-zagged configuration. The device can also include any number of springs, and the springs can be arranged around the perimeter of the device. A person skilled in the art will appreciate that the spring(s) can be formed from a variety of materials, including the same materials as the rings as well as biocompatible metals such as titanium, stainless steel, nitinol, elastomeric materials, and combinations thereof.

FIG. 16 illustrates another embodiment of a device having first and second rings 1090, 1091 that are connected by at least one strut or tube 1094. The tubes can have a variety of sizes, and they can be solid or they can have holes formed therein. Similar to the device above, the device can include any number of tubes and the tubes can be arranged in a variety of configurations around the perimeter of the central opening of the rings. Additionally, the tubes can be formed from the same materials as the rings and/or biocompatible metals such as titanium, stainless steel, nitinol, elastomeric materials, and combinations thereof.

In another embodiment, as shown in FIG. 17, the first and second rings 1190, 1191 can be connected by at least one layer of mesh material. As shown, the rings 1190, 1191 are connected by two layers of mesh material 1196, 1198 that form first and second walls that are spaced apart from one another. Exemplary mesh mating elements and materials are discussed in more detail below. The mesh allows the nucleus disc replacement implant to be injected through and to interlock with the device. A person skilled in the art will appreciate the variety of techniques that can be used to connect multiple rings to one another.

In use, the devices illustrated in FIGS. 15-17 can be biased to the expanded ring-shaped configuration as described above with respect to FIGS. 1-5. A force can be applied to the device to bring the opposed walls of the device towards one another to move the device to the compressed configuration. Upon release of the force, the device can return to its original expanded configuration.

Figure 18:
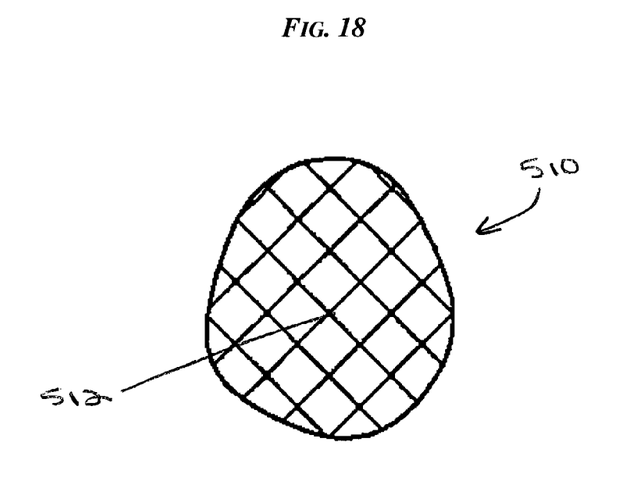
FIG. 18 is a top view of another embodiment of a nucleus anti-expulsion device formed from a mesh material and having a substantially spherical shape.

FIG. 18 illustrates another embodiment of an anti-expulsion device 510 having a body 512 that is formed of a mesh material. While the body 512 can have a variety of shapes, it is preferably three dimensional, such as spherical, semi-spherical, rectangular, square, etc. The body can also optionally include inner and outer mesh walls that are connected by mesh sidewalls to form a hollow three-dimensional body. Alternatively, the space between the walls can include one or more layers of mesh material. A person skilled in the art will appreciate that the body can have a variety of shapes and sizes, but it is preferably adapted to fit within a nucleus void of a spinal disc. A person skilled in the art will also appreciate that the body can be formed from a variety of bioimplantable and flexible materials such as cloth or mesh, such as Teflon, polyurethane, nylon, precured silicone, polyethylene terephthalate (PET-Dacron), other polymeric or metallic fibers, and combinations thereof. Also similar to the devices disclosed above, the body can also include radiopaque materials in order to facilitate visualization and/or regenerative materials for facilitating regeneration of the annular wall.

In use, the device 510 can be movable between a compressed configuration for insertion through an opening of an annular wall and into a nucleus void, and an expanded configuration for release once positioned within the nucleus void. Similar to the devices above in FIGS. 10A-17, the device 510 is biased to the expanded configuration, where it is substantially spherical. As a result of the application of a force, opposed sidewalls of the device 510 can be brought towards one another in the compressed configuration. In an exemplary embodiment, the device is biased to the expanded configuration, where it is substantially spherical or otherwise three-dimensional. A compressive force can be applied to the body to compress opposed sidewalls towards one another, thereby allowing the body to fit through an opening in an annulus.

Figure 21A:
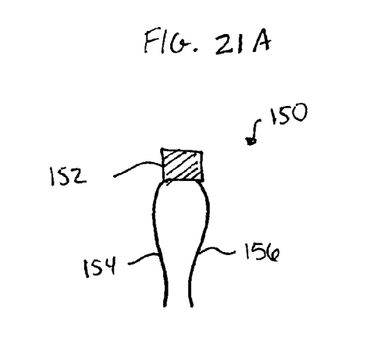
FIG. 21A is a top view of another embodiment of a nucleus anti-expulsion device having a plug and opposed legs, showing the device in the compressed configuration.
Figure 21B:
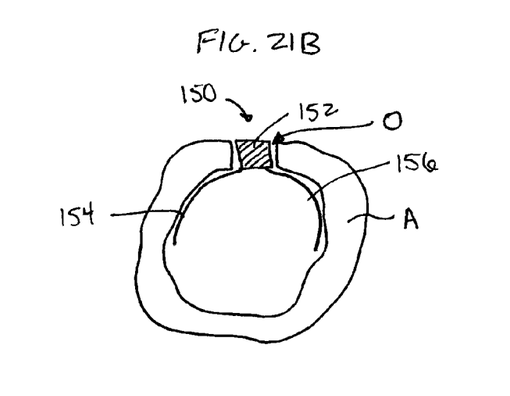
FIG. 21B is a top view of the device of FIG. 21A implanted within a nucleus void and showing the plug positioned within an opening formed in the annulus and the legs in the expanded position to engage the inner wall of the annulus.

In other embodiments, the anti-expulsion device can include a plug that is adapted to fill the opening extending through the annulus, and opposed arms or legs that are adapted to be positioned within the nucleus void and to abut against an inner surface of the annular wall to prevent expulsion of the anti-expulsion device from the nucleus void. FIGS. 21A and 21B illustrate one exemplary embodiment of such an anti-expulsion device 150. As shown, the device 150 includes a plug 152 and opposed legs 154, 156 coupled to and extending from the plug. The plug 152 can have various shapes and sizes, but it is preferably adapted to fit within an opening formed in an annular wall. In an exemplary embodiment, the plug is substantially cylindrical. The plug can also be formed from a variety of materials, including those previously disclosed herein for enhancing annular wall restoration, as well as the various other materials disclosed therein. The legs 154, 156 can also vary in shape and size, but they are preferably shaped to rest against and extend around at least a portion of an inner wall of an annulus, or an inner wall created by a nucleus void. As shown in FIG. 21A, each leg 154, 156 has a generally elongate curved configuration. The legs 154, 156 are also preferably movable between a compressed position as shown in FIG. 21A, and an expanded position as shown in FIG. 21B. In the compressed position, the terminal ends of the legs 154, 156 are brought toward one another such that the device 10 has a generally elongate configuration to allow it to be inserted through an insertion instrument, such as a cannula. In the expanded position, the legs 154, 156 are moved away from one another and together can have a generally c-shaped configuration. The legs 154, 156 can be movably coupled to the plug 152 using a variety of techniques. The legs 154, 156 are also preferably biased to the expanded configuration such that they can self-expand when released from an insertion device. In use, the device 150 is introduced legs-first through an opening O formed in an annulus A to position the plug 152 within the opening O, as shown in FIG. 21B. The legs 154, 156 will move away from one another to the expanded position, thereby engaging the inner wall of the annulus A, or engaging an inner wall created by a nucleus void. A nucleus disc replacement implant can be introduced into the nucleus void either prior to or after insertion of the implant 150. Where the nucleus disc replacement implant is one that is injected into the nucleus void after the implant 150 is positioned, the plug 152 can optionally include a lumen or bore formed therethrough for allowing the nucleus disc replacement implant to be injected into the nucleus void.

Figure 19A:
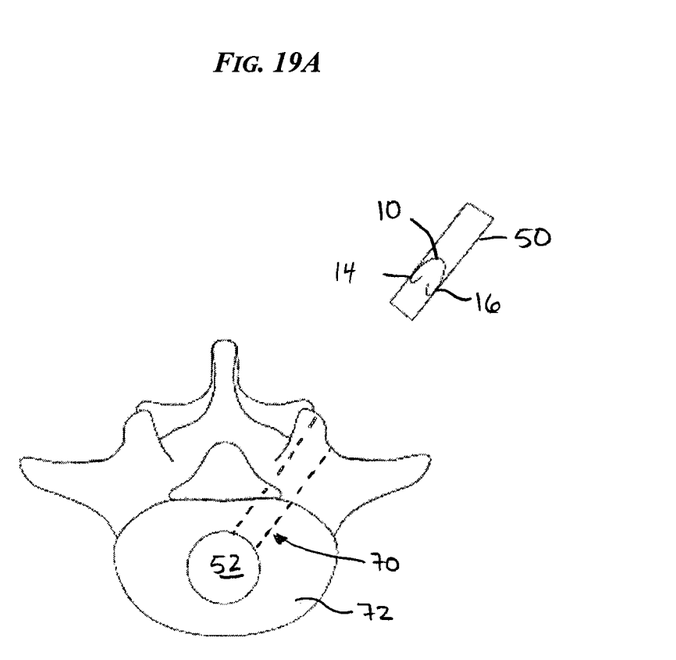
FIG. 19A is a top view of a vertebral body showing the device of FIG. 1 disposed within a cannula prior to insertion of the device into an annulus of a spinal disc.
Figure 19B:
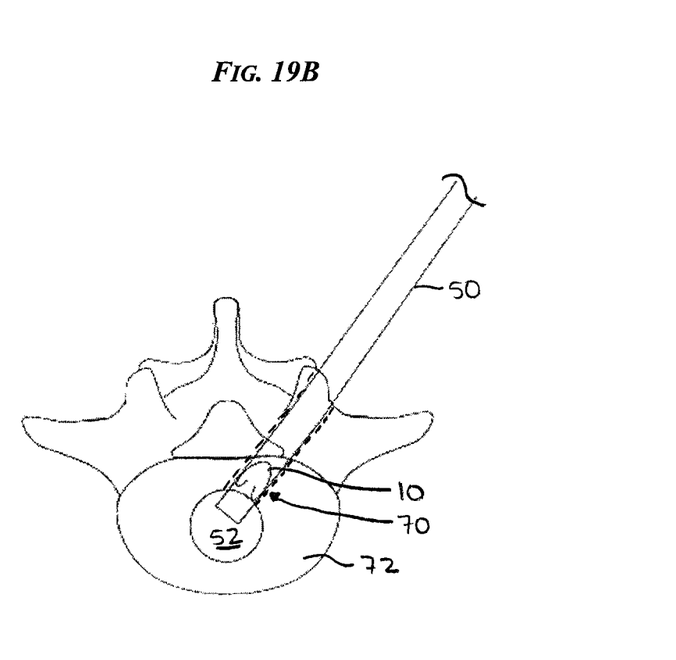
FIG. 19B is a top view of the vertebral body, cannula, and device of FIG. 19A, showing the cannula positioned through an opening formed in the annulus of the spinal disc.
Figure 19C:
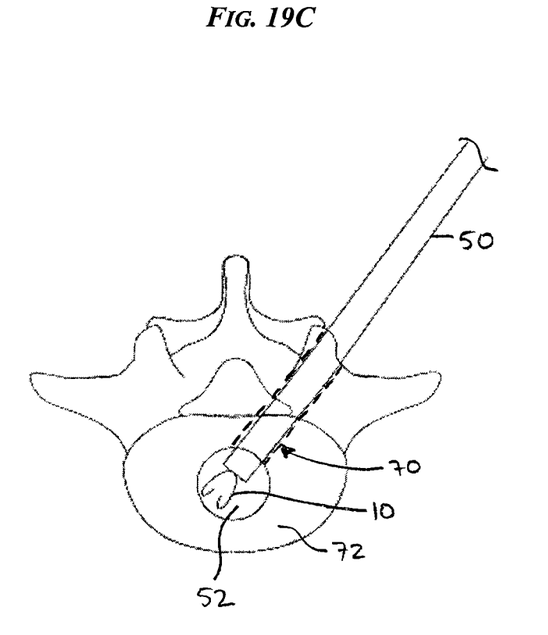
FIG. 19C is a top view of the vertebral body, cannula, and device of FIG. 19B, showing the device being released from the cannula and into the annulus of the spinal disc.
Figure 19D:
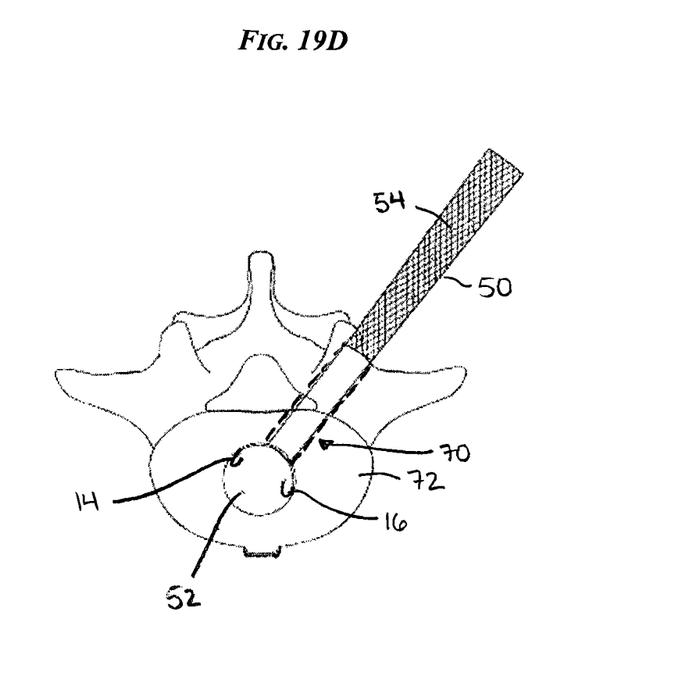
FIG. 19D is a top view of the vertebral body, cannula, and device of FIG. 19C, showing the device positioned within the annulus of the spinal disc.

The present invention also provides various methods for implanting a nucleus disc replacement implant. In one exemplary embodiment, the natural nucleus can be replaced by forming a small opening in the annulus of a spinal disc and removing a portion or all of the natural nucleus to form a nucleus void. Various techniques are known in the art and can be used for forming an opening and removing the nucleus. Once the nucleus void is prepared, the anti-expulsion device can be introduced therein. In an exemplary embodiment, as shown in FIGS. 19A-19F, the device 10 is introduced through the opening 70 previously formed in the annulus 72. This can be achieved by compressing the device 10 so that it has a maximum width that is smaller than a size of the opening. As shown in FIG. 19A, a cannula 50 having a size that is the same as or less than the opening 70 is used to compress the device 10. The cannula 50 will cause the distal ends 14, 16 of the device 10 to move toward one another. As shown in FIG. 19B, the cannula 50 can be inserted through the opening 70 in the annular wall 72. The device 10 can then be advanced through the cannula 50 and into a nucleus void 52 of the spinal disc, as shown in FIG. 19C. While the exemplary embodiment illustrates a cannula 50 that is used to insert the device 10 into the nucleus void 52, a person skilled in the art will appreciate that the device 10 can be inserted into the nucleus void 52 using a variety of other devices and techniques, and the technique can vary depending upon the particular procedure performed. Once within the nucleus void 52, the device 10 can self-expand or other tools can be used to move the device to the expanded configuration. Once expanded, as shown in FIG. 19D, the distal ends 14, 16 of the device 10 will move away from one another such that the device 10 has a width that is greater than the size of the opening 70 in the annular wall 72.

Figure 19E:
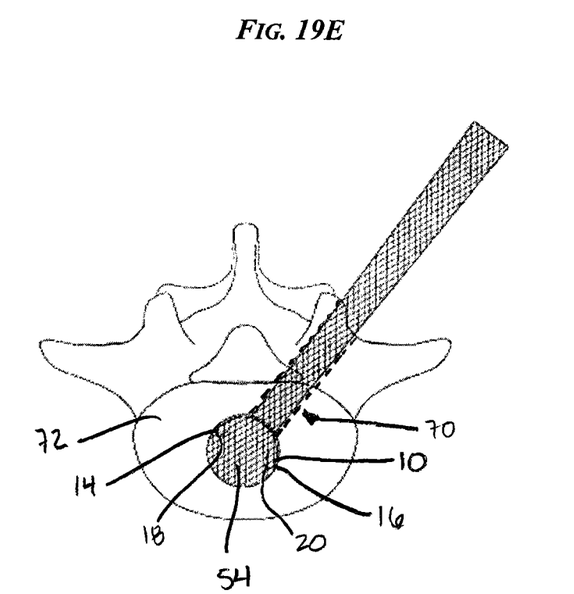
FIG. 19E is a top view of the vertebral body, cannula, and device of FIG. 19D, showing the introduction of a nucleus disc replacement implant into the annulus of the spinal disc.
Figure 19F:
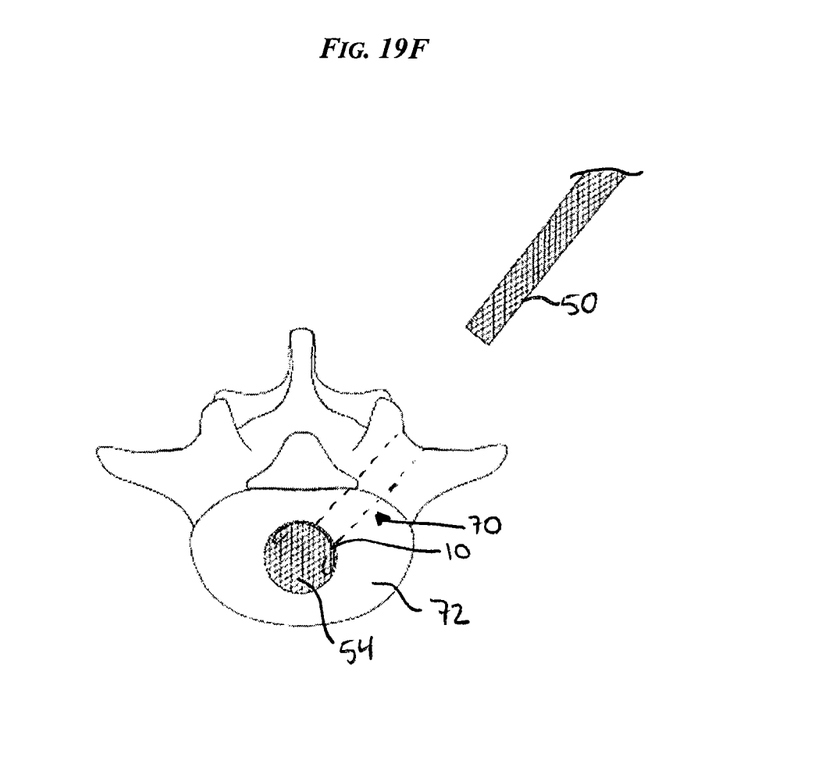
FIG. 19F is a top view of the vertebral body, cannula, and device of FIG. 19E, showing the cannula removed and the device and the nucleus disc replacement implant filling the void created by the removed nucleus.

As further shown in FIG. 19D, the nucleus disc replacement implant 54 can be introduced into the nucleus void 52 using, for example, the same cannula 50 that was used to insert the anti-expulsion device 10. As the nucleus disc replacement implant 54 is inserted into the nucleus void 52, it will flow around, over, and/or through the anti-expulsion device 10, as shown in FIGS. 19E-19F. For example, where the anti-expulsion device 10 is substantially C-shaped, the mating elements 18, 20 at the distal ends 14, 16 of the device 10 can be surrounded and captured by the nucleus disc replacement implant 54 and thereby encapsulate the mating elements 18, 20. As the implant 54 cures, the anti-expulsion device 10 interlocks with and becomes integral with the implant 54. This prevents the implant 54 from migrating within the annulus 52 or being expulsed through the opening 70 in the annular wall 72. The device can also optionally be pushed by expansion of the nucleus replacement implant 10 towards the opening 70 in the annular wall 72 either before or after the introduction of the nucleus disc replacement implant 54 to allow the device 10 to reinforce the annular wall. As previously discussed, the anti-expulsion device 10 can also optionally include regenerative material to facilitate regeneration of the annulus 72 and thereby close the opening 70. Once the implant 54 is inserted into the nucleus void 52 and the device 10 is positioned as desired, the cannula 50 can then be removed from the opening 70 in the annular wall 72 and the opening 70 can optionally be closed.

Figure 20A:
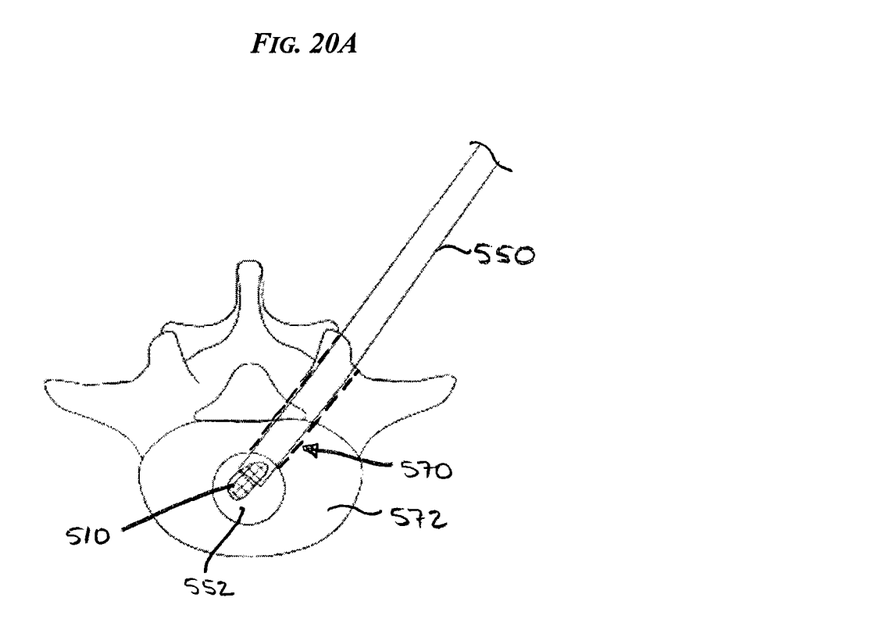
FIG. 20A is a top view of a vertebral body showing the device of FIG. 18 disposed within a cannula prior to insertion of the device into the void created by the removed nucleus of a spinal disc.
Figure 20B:
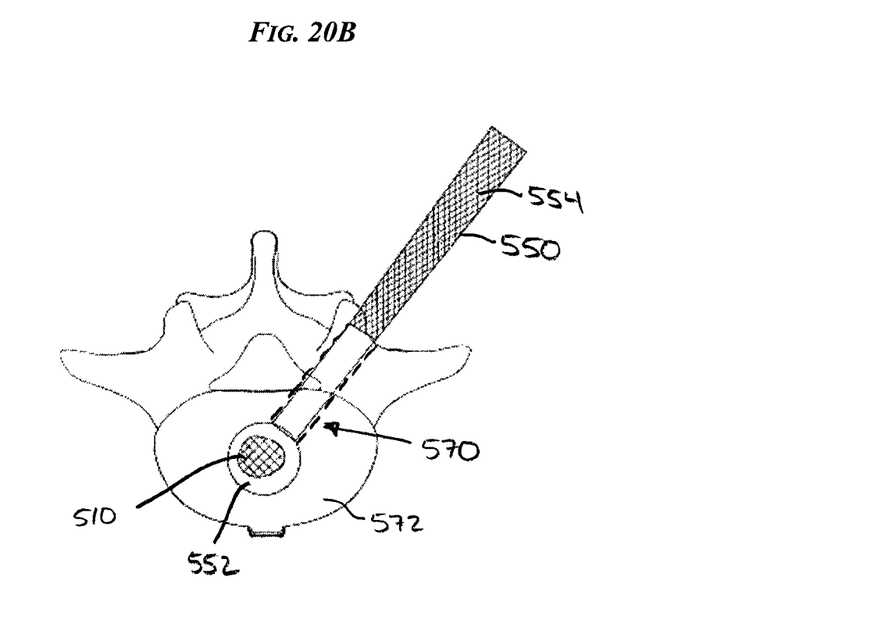
FIG. 20B is a top view of the vertebral body, cannula, and device of FIG. 20A, showing the device positioned within the void created by the removed nucleus of the spinal disc, and a nucleus disc replacement implant being introduced into the annulus of the spinal disc.
Figure 20C:
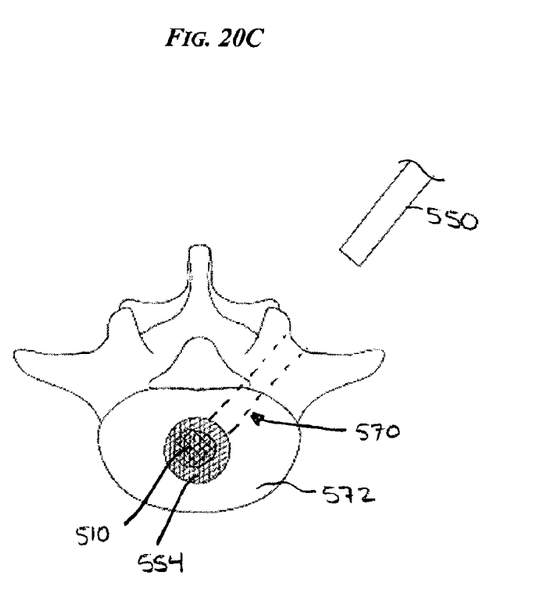
FIG. 20C is a top view of the vertebral body, cannula, and device of FIG. 20B, showing the final placement of the nucleus disc replacement implant into the void created by the removed nucleus of the spinal disc.

FIGS. 20A-20C illustrate another exemplary method for implanting a nucleus disc replacement implant 554. The method is similar to the method described above with respect to FIGS. 19A-19F. Once the space within the nucleus is prepared, i.e., the nucleus void is created, the anti-expulsion device can be introduced therein. In an exemplary embodiment, as shown in FIG. 20A, the device 510 is introduced through the opening 570 previously formed in the annulus 552. This can be achieved by compressing the device 510 so that it has a maximum size that is smaller than a size of the opening 570. As shown in FIG. 20A, the device 510 is compressed to have a kidney-bean shape by inserting it into a cannula 550 having a size that is the same as or less than the size of the opening 570. The device 510 can then be advanced through the cannula 550 and into the nucleus void 552.

Once within the nucleus void 552, the device 510 can self-expand to the expanded configuration. Alternatively, a tool can be used to cause the device 510 to move from the compressed configuration to the expanded configuration. The device 510 now has a size that is greater than the size of the opening 570 in the annulus 572. A nucleus disc replacement implant 554 can also be introduced into the nucleus void 552, as shown in FIG. 20B. As the nucleus disc replacement implant 554 enters the nucleus void 552, it travels into, around, and through the holes in the mesh of the anti-expulsion device 510. Once the implant 554 cures, the anti-expulsion device 510 and the implant 554 will interlock and become integral with one another, as shown in FIG. 20C. The implant will now fill the nucleus void 552 such that it cannot migrate within the nucleus void. The implant is also prevented from being expulsed from the opening 570 in the annulus 572. The device can also optionally be pushed towards the opening 570 in the annulus 572 either before or after the introduction of the nucleus disc replacement implant to allow the device to reinforce the annular wall. As previously discussed, the anti-expulsion device can also optionally include regenerative material to facilitate regeneration of the annulus and thereby close the opening 570. Once the implant 554 is inserted into the nucleus void 552 to fill the nucleus void and the device 510 is positioned as desired, the insertion tool 550 can then be removed from the opening 570 in the annulus 572 and the opening 570 can optionally be closed.

While the exemplary embodiments illustrate the anti-expulsion device being inserted through the annulus to fill the nucleus void prior to the insertion of the nucleus disc replacement implant, a person skilled in the art will appreciate that the nucleus disc replacement implant can be inserted into the nucleus void prior to insertion of the anti-expulsion device. Once the implant has been inserted, and preferably prior to the curing thereof, the anti-expulsion device can be inserted into the nucleus void and brought into contact with the nucleus disc replacement implant. As the implant cures it can interlock with mating elements on the anti-expulsion device to become integral therewith, such that the device and implant are prevented from migrating with or expulsing from the opening in the annular wall. Alternatively, the anti-expulsion device and nucleus disc replacement implant can be inserted into the nucleus void simultaneously using, for example, a cannula/syringe system. A pre-cured material can be used. For example, the device of FIG. 5 is particularly advantageous for use with a pre-cured material, as the spikes 318, 320 can penetrate into the implant. As previously indicated, the anti-expulsion device can interlock with the annular wall, rather than or in addition to interlocking with the nucleus disc replacement implant, to prevent expulsion of the implant.

A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An anti-expulsion device, comprising:
   a c-shaped body movable between a compressed configuration in which the body is adapted to fit through an opening in an annulus of a spinal disc with first and second ends of the body being moved toward one another and toward a center of the body, and an expanded configuration in which the body is configured to have a size larger than a size of the opening in the annulus of the spinal disc, and in which the first and second ends are moved away from one another and away from the center of the body, the body in the compressed configuration and in the expanded configuration including a discrete, bulbous mating feature formed on the first and second ends of the body; and
   a nucleus disc replacement implant that encapsulates the mating feature on the body such that inside the annulus of the spinal disc the body becomes integral with the nucleus disc replacement implant to prevent expulsion of the nucleus disc replacement implant from the annulus of the spinal disc.

2. The device of claim 1, wherein the mating feature is selected from the group consisting of curls, hooks, undercuts, penetrating legs, staples, coils, barbs, channels, holes, claws, and combinations thereof.

3. The device of claim 1, wherein the body includes at least one bend region that facilitates movement of the body from the compressed configuration to the expanded configuration.

4. The device of claim 3, wherein the bend region is formed at a mid-portion of the body such that the first and second ends move toward one another in the compressed configuration.

5. The device of claim 1, wherein the body includes a bioactive tissue regenerative material attached thereto.

6. The device of claim 1, wherein the body is adapted to reinforce an annular wall of an annulus of a spinal disc when the body is in the expanded configuration.

7. The device of claim 1, further comprising a plug adapted to be positioned within an opening in an annulus, and wherein the body includes legs coupled to the plug and adapted to be disposed within and to engage an inner wall of an annulus.

8. The device of claim 1, wherein the c-shaped body has an S-shaped cross-sectional shape.

9. The device of claim 1, wherein the c-shaped body has a cross-sectional shape with a planar surface and a curved surface.

10. A nucleus disc replacement system, comprising:
    a nucleus disc replacement implant; and
    a c-shaped anti-expulsion device having a body having a mating feature formed on first and second ends of the body, the body being movable between a compressed configuration in which the body having the c-shape and having the mating feature formed on first and second ends of the body is adapted to fit through an opening in an annulus of a spinal disc, and in which the first and second ends are moved toward a mid-portion of the anti-expulsion device, and an expanded configuration in which the body having the c-shape and having the mating feature formed on first and second ends of the body is configured to have a size larger than a size of an opening in an annulus of a spinal disc, and in which the first and second ends are moved away from the mid-portion of the anti-expulsion device, the nucleus disc replacement implant encapsulating the mating feature on the body such that following insertion of the device through the opening the device prevents expulsion of the nucleus disc replacement implant through an annulus of a spinal disc, and
    wherein the body includes opposed legs movable between the compressed and expanded configurations, and a plug coupled to the legs and adapted to be positioned within an opening in an annulus to interlock with the annulus.

11. The system of claim 10, wherein the mating feature is selected from the group consisting of curls, hooks, undercuts, penetrating legs, staples, coils, barbs, channels, holes, claws, and combinations thereof.

12. The system of claim 10, wherein at least a portion of the body includes a bend region that is adapted to allow the body to move from the compressed configuration to the expanded configuration.

13. The system of claim 12, wherein the bend region is formed at the mid-portion of the body such that the first end of the body is moved toward the second end of the body when in the compressed configuration.

14. The system of claim 10, wherein the body is adapted to reinforce an annular wall of an annulus of a spinal disc when the body is in the expanded configuration.

15. A nucleus disc replacement system, comprising:
    a nucleus disc replacement implant; and
    a c-shaped anti-expulsion device having a body having a mating feature formed on first and second ends of the body, the body being movable between a compressed configuration in which the body having the c-shape and having the mating feature formed on first and second ends of the body is adapted to fit through an opening in an annulus of a spinal disc, and in which the first and second ends are moved toward a mid-portion of the anti-expulsion device, and an expanded configuration in which the body having the c-shape and having the mating feature formed on first and second ends of the body is configured to have a size larger than a size of an opening in an annulus of a spinal disc, and in which the first and second ends are moved away from the midportion of the anti-expulsion device, the nucleus disc replacement implant encapsulating the mating feature on the body such that following insertion of the device through the opening the device prevents expulsion of the nucleus disc replacement implant through an annulus of a spinal disc wherein the body includes a tissue regenerative material attached thereto.

16. A method for implanting a nucleus disc replacement implant, comprising:
inserting an anti-expulsion device having a mating feature formed on first and second ends of the anti-expulsion device through an opening formed in an annulus of a spinal disc to position the anti-expulsion device within a nucleus void formed in a nucleus of the spinal disc, wherein during insertion, the anti-expulsion device is in a compressed configuration in which the first and second ends are moved toward one another and toward a center of the anti-expulsion device, and in which the anti-expulsion device is c-shaped;
releasing a force on the anti-expulsion device such that it moves from the compressed configuration to an expanded configuration in which the first and second ends move away from one another and away from the center of the anti-expulsion device, in which the anti-expulsion device is c-shaped, and in which the anti-expulsion device having the mating feature formed on the first and second ends thereof has a size greater than a size of the opening in the annulus; and
inserting a nucleus disc replacement implant into the nucleus void, the nucleus disc replacement implant encapsulating the mating feature formed on first and second ends of the anti-expulsion device in the nucleus void such that the anti-expulsion device prevents expulsion of the nucleus disc replacement implant through the opening.

17. The method of claim 16, wherein the anti-expulsion device interlocks with the annulus.

18. The method of claim 16, wherein the anti-expulsion device is inserted through a cannula that compresses the anti-expulsion device into the compressed configuration, and wherein releasing the force comprises advancing the anti-expulsion device out of the cannula and into the nucleus void.

19. The method of claim 18, wherein the first and second ends are in contact with one another when the anti-expulsion device is in the cannula in the compressed configuration.

20. The method of claim 16, further comprising positioning the anti-expulsion device against the opening in the annulus to act as a reinforcement of an annular wall.

21. The method of claim 16, wherein the anti-expulsion device includes a tissue regenerative material, and the method further comprises positioning the anti-expulsion device against the opening in the annulus such that the tissue regenerative material facilitates regeneration of an annular wall.

22. The method of claim 16, further comprising, prior to inserting the anti-expulsion device, removing at least a portion of a nucleus from a spinal disc to form the nucleus void.

23. The system of claim 10, further comprising a cannula configured to be introduced through an opening in an annulus of a spinal disc, the body in the compressed configuration being disposed in the cannula with the first and second ends of the body moved toward one another.

24. The system of claim 23, wherein the first and second ends of the body are in contact with one another with the body in the compressed configuration within the cannula.

* * * * *